United States Patent [19]

D'Amico

[11] 3,992,191
[45] Nov. 16, 1976

[54] N,N'-(O-PHENYLENEDIMETHYLIDYNE)-BIS-SUBSTITUTED ANILINES

[75] Inventor: John J. D'Amico, St. Louis, Mo.

[73] Assignee: Monsanto Company, St. Louis, Mo.

[22] Filed: Nov. 28, 1975

[21] Appl. No.: 636,000

[52] U.S. Cl. .............................. 71/121; 260/566 F
[51] Int. Cl.² ........................................ C07C 119/00
[58] Field of Search .................. 260/566 F; 71/121

[56] References Cited
UNITED STATES PATENTS

| | | | |
|---|---|---|---|
| 3,210,422 | 10/1965 | Holsten et al. | 260/566 |
| 3,567,718 | 3/1971 | Elslager | 260/566 |
| 3,697,589 | 10/1972 | Menasse et al. | 260/566 |

Primary Examiner—Gerald A. Schwartz
Attorney, Agent, or Firm—Richard H. Shear; Donald W. Peterson

[57] ABSTRACT

Bis-Schiff bases having the formula

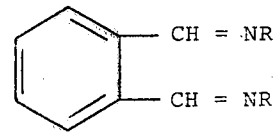

are effective plant growth regulants.

12 Claims, No Drawings

N,N'-(O-PHENYLENEDIMETHYLIDYNE)-BIS-SUBSTITUTED ANILINES

This invention relates to novel chemical compounds used to regulate the natural growth or development of plants by means of a chemical treatment. More specifically, the invention is directed to a method whereby the natural growth or development of leguminous plants, such as soybeans, is regulated by applying to said plants a bis-Schiff base having the structure of formula I

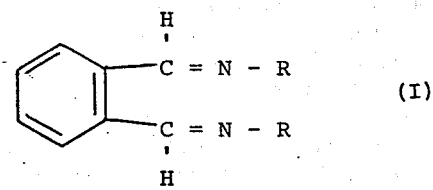

where R is

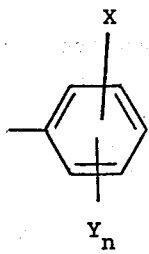

X and y are independently methoxy, trifluoromethyl or chloro; and $n$ is zero or one.

As used herein, the regulation of "plant growth or development" is understood to mean the modification of the normal sequential development of a treated plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color is illustrative of higher chlorophyll activity indicative of improved rate of photosynthesis.

Although phytotoxic amounts of the active ingredient may be employed to exert a herbicidal effect, the regulation of plant growth in accordance with the present invention does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

By the term active ingredient is meant the active bis-Schiff bases of the foregoing formula.

A preferred embodiment of the invention is those bis-Schiff bases in which X is located at the 3 position of the ring and X and Y are selected from the group consisting of methoxy and trifluoromethyl. Most preferably, Y will be located at the 5 position of the ring. For example, X and Y being methoxy at the 3 and 5 positions of the ring is a preferred compound as is that compound in which X is trifluoromethyl at the 3 position and n is zero.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent or emulsifying agent or any suitable combination of these.

Illustrative finely divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray. Should the application of the plant growth composition to the plant growth medium be desired, this is accomplished by incorporating the compositions in the soil or other media in the area where modification of the plants is desired.

The quantity of active ingredient in the plant growth regulating composition varies depending upon the type of formulation, rate of application, plant to be treated, etc. Compositions of this invention generally contain from about 5 to 95 parts active ingredient, about 1 to 50 parts surface-active agent and about 4 to 94 parts solvent, all parts being by weight based on the total weight of the composition. The specific quantity of active ingredient to be utilized, however, is well within the skill of the art.

In selecting the appropriate rate of application of the active ingredient, it will be recognized that precise rates will also be dependent upon the mode of application, such as soil incorporation, band application, preplant seed treatment and various other factors known to those skilled in the art. In foliar treatment for the regulation of plant growth, the active ingredients are applied in amounts of from about 0.056 to about 11.2 or more kilos per hectare. Preferred are foliar applications of from 0.056 to 5.6 kilos of the active ingredient per hectare. In application to the soil habitat of germinant seeds, emerging seedlings and established vegetation for the regulation of plant growth, the active ingredients are applied in amounts of from 0.0112 to about 22.4 kilos per hectare or more. The application to the soil of from 0.112 to about 11.2 kilos of active ingredient per hectare is preferred. Foliar application to plants beginning to blossom are preferred over other types of applications.

As illustrated by the following examples, certain bis-Schiff bases are found to be effective growth regulators for leguminous plants, as represented by soybean (Glycine max). Significant differences between those legumes treated with the active ingredient and those not treated are found to occur. Among the differences found are a reduction in stature of the treated legume, an alteration in canopy shape and axillary bud development.

In accordance with the present invention, various plant growth regulating compositions were formulated so that they could be applied in tests at a rate the equivalent of 200 gallons per acre. TABLE I illustrates the formulation of the composition for several application rates of active ingredient. In each formulation, the stock solution utilized is 1 percent of the active ingredient dissolved in acetone.

TABLE I

| RATE Lbs/Acre (kilos/hectare) | ml. of 1% Stock Solution | ml. Acetone | ml. 0.39% TWEEN 20 In Water As Surfactant |
| --- | --- | --- | --- |
| 6.0 (6.72) | 2.0 | — | 3.6 |
| 3.0 (3.26) | 1.0 | 1.0 | 3.6 |
| 1.2 (1.34) | 0.4 | 1.6 | 3.6 |
| 0.6 (.672) | 0.2 | 1.8 | 3.6 |
| 0.3 (.336) | 0.1 | 1.9 | 3.6 |

EXAMPLE 1

A number of soybean plants, variety Corsoy, are grown from seeds in aluminum pans in the greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition as formulated in accordance with TABLE I is then applied to the pan of growing plants by overhead spray at a rate equivalent to the desired rate of active ingredient per acre. The treated pans, along with the control pans, are maintained in a greenhouse and watered from below on a sand bench and fertilized with a uniform portion of a water-soluble balanced fertilizer.

Two weeks after application of the chemical, the average height of the soybean plants in the treated pan is again measured as above and the difference in the average height before and two weeks after application represent the increase in the development of the treated pans. This development in growth of the treated plants is compared to the average increase in growth of the plants in the control pans during the same period of time. A variation of 25 percent or more in the development of at least two-thirds of the treated plants when compared to the development of the control plants demonstrates that the chemical is an effective plant regulant. Thus, a chemical is considered active when the treated plants manifest a decrease in growth of at least 25 percent less than that of the control plants, i.e., stature reduction, or an increase in growth in excess of 25 percent of that of the control plants, i.e., growth stimulation.

When the active ingredient utilized was a bis-Schiff base having the following formula

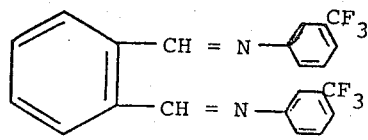

the following responses were noted at the indicated rate.

| RATE Lbs/Acre (kilos/hectare) | Response |
| --- | --- |
| 6.0 (6.72) | Stature reduction, axillary bud development, altered canopy |
| 6.0 (6.72) | Stature reduction, axillary bud development, rosette growth, chlorosis, slight leaf burn |
| 3.0 (3.36) | Stature reduction, axillary bud development, rosette growth, altered canopy, chlorosis |
| 1.2 (1.34) | Stature reduction, axillary bud development, altered canopy, chlorosis |

EXAMPLE 2

The procedure of Example 1 was repeated utilizing

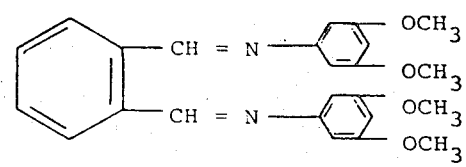

as the active ingredient. The responses noted are as follows.

| RATE Lbs/Acre (kilos/hectare) | Response |
|---|---|
| 6.0 (6.72) | Stature reduction, axillary bud development, stem distortion, rosette growth |
| 3.0 (3.36) | Stature reduction, axillary bud development, stem distortion, rosette growth |
| 1.2 (1.34) | Stature reduction, axillary bud development, stem distortion, rosette growth |
| 0.6 (.672) | Stature reduction, axillary bud development, rosette growth |
| 0.3 (.336) | Stature reduction, axillary bud development, rosette growth |

EXAMPLE 3

Individual soybean plants, variety Corsoy, are grown from seed in 6-inch pots containing a good grade of top soil. Two pots of 6-week old plants (5-6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and are fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15% in the average total height of the treated plants, when compared to the average total height of the control plants, demonstrates that the chemical is an effective plant growth regulator. Utilizing

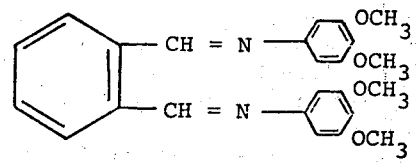

as the active ingredient, the following responses were noted at their respective rates.

| RATE Lbs/Acre (kilos/hectare) | Response |
|---|---|
| 0.250 (0.280) | Stature reduction, leaf distortion, rosette growth |
| 0.100 (0.112) | Stature reduction, leaf alteration, chlorosis |
| 0.050 (0.056) | Stature reduction, early pod set |

Generally, the bis-Schiff bases of the invention are prepared by reacting the appropriate substituted aniline and o-phthalicdicarboxaldehyde. More particularly, the bis-Schiff bases are prepared by heating at reflux for four hours a stirred mixture containing 0.4 moles of the appropriate substituted aniline, 0.2 moles of o-phthalicdicarboxaldehyde, 2 grams of p-toluenesulfonic acid and 200 ml. of toluene. During the heating, 7.6 ml. of water and 120 ml. of toluene are removed via a Dean Stark condenser. After allowing the stirred reaction mixture to cool to room temperature, 100 ml. of heptane is added and stirring continued at 0°–10° C. for 30 minutes. The solid may be collected by filtration, washed with water and air dried.

Table II, below, illustrates the analytical data obtained when the above procedure was utilized to prepare the bis-Schiff bases having the formula

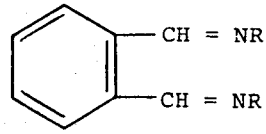

TABLE II

| R | mp.° C. | Yield | % C Calcd. | % C Found | % H Calcd. | % H Found | % N Calcd. | % N Found | % F Calcd. | % F Found |
|---|---|---|---|---|---|---|---|---|---|---|
| 3,4-(OCH₃)₂-phenyl | 154–5 [a] | 62 | 71.27 | 71.44 | 5.98 | 6.09 | 6.93 | 6.81 | | |
| 3-CF₃-phenyl | 147–8 [b] | 57 | 62.86 | 63.05 | 3.36 | 3.42 | 6.66 | 6.54 | 27.12 | 26.92 |
| 3-Cl-phenyl | 53–5 | 99 | 54.01 | 54.18 | 2.47 | 2.47 | 5.73 | 5.61 | | |
| 3,5-(CF₃)₂-phenyl | 159–60 [c] | 36 | 51.81 | 51.86 | 2.17 | 2.08 | 5.04 | 4.96 | 40.98 | 41.12 |

TABLE II-continued

| R | mp.° C. | Yield | % C Calcd. | % C Found | % H Calcd. | % H Found | % N Calcd. | % N Found | % F Calcd. | % F Found |
|---|---|---|---|---|---|---|---|---|---|---|
| 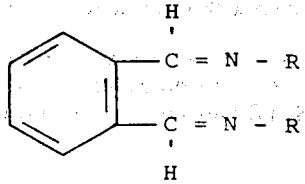 | 204–5 [d] | 32 | 56.91 | 57.03 | 2.87 | 2.93 | 6.64 | 6.50 | | |
| 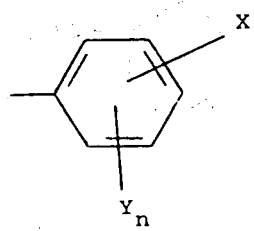 | 68–70 | 99 | 54.01 | 53.77 | 2.47 | 2.58 | 5.73 | 5.61 | | |

[a] Recrystallization from ethyl acetate
[b] Recrystallization from heptane-isopropyl alcohol (3:1)
[c] Recrystallization from isopropyl alcohol
[d] Recrystallization from toluene Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

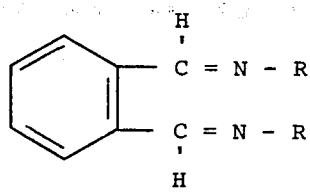

wherein R is

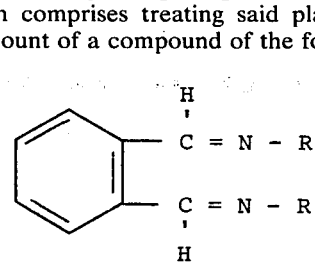

X and Y are independently selected from the group consisting of methoxy, trifluoromethyl and chloro; and n is zero or 1.

2. A compound according to claim 1 wherein X and Y are selected from the group consisting of methoxy and trifluoromethyl and X is located at the 3 position of the ring.

3. A compound according to claim 2 wherein X is trifluoromethyl and n is zero.

4. A compound according to claim 2 wherein X and Y are methoxy, n being 1.

5. A compound according to claim 4 wherein Y is in the 5 position.

6. A method of regulating the growth of leguminous plants which comprises treating said plants with an effective amount of a compound of the formula

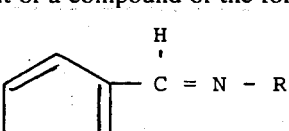

wherein R is

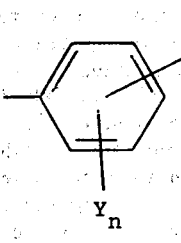

X and Y are independently selected from the group consisting of methoxy, trifluoromethyl and chloro; and n is zero or 1.

7. A method according to claim 6 wherein X and Y are selected from the group consisting of methoxy and trifluoromethyl and X is located at the 3 position on the ring.

8. A method according to claim 7 wherein X is trifluoromethyl and n is zero.

9. A method according to claim 7 wherein X and Y are methoxy, n being 1.

10. A method according to claim 9 wherein Y is in the 5 position.

11. A method according to claim 5 wherein said plants are soybean.

12. A composition for regulating the growth of leguminous plants which comprises from about 5 to 95 parts by weight of a compound of the formula

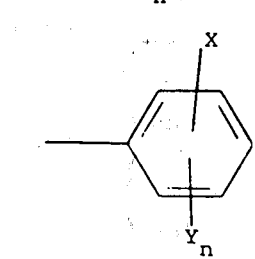

wherein R is

X and Y are independently selected from the group consisting of methoxy, trifluoromethyl and chloro, and n is zero or 1; the remaining parts being composed of one or more suitable carriers, diluents and/or adjuvants.

* * * * *